US012667703B2

(12) United States Patent
Neustadter et al.

(10) Patent No.: US 12,667,703 B2
(45) Date of Patent: Jun. 30, 2026

(54) FLEXIBLE SECURE CONNECTION OF MULTIPLE GUIDEWIRES

(71) Applicant: CARDIAC SUCCESS LTD., Yokneam (IL)

(72) Inventors: David Neustadter, Nof Ayalon (IL); Boaz Manash, Zichron Yaakov (IL)

(73) Assignee: CARDIAC SUCCESS LTD., Yokneam (IL)

( * ) Notice: Subject to any disclaimer, the term of this patent is extended or adjusted under 35 U.S.C. 154(b) by 989 days.

(21) Appl. No.: 17/797,326

(22) PCT Filed: Feb. 16, 2021

(86) PCT No.: PCT/IB2021/000087
§ 371 (c)(1),
(2) Date: Aug. 3, 2022

(87) PCT Pub. No.: WO2021/161102
PCT Pub. Date: Aug. 19, 2021

(65) Prior Publication Data
US 2023/0062364 A1 Mar. 2, 2023

Related U.S. Application Data

(60) Provisional application No. 62/977,271, filed on Feb. 16, 2020.

(51) Int. Cl.
*A61M 25/09* (2006.01)

(52) U.S. Cl.
CPC ............... *A61M 25/0905* (2013.01); *A61M 2025/09083* (2013.01); *A61M 2025/09141* (2013.01); *A61M 2025/09166* (2013.01)

(58) Field of Classification Search
CPC .... A61M 25/0905; A61M 2025/09083; A61M 2025/09141; A61M 2025/09166; A61M 2025/09175; A61M 25/09
See application file for complete search history.

(56) References Cited

U.S. PATENT DOCUMENTS

| | | | |
|---|---|---|---|
| 3,955,578 A | 5/1976 | Chamness et al. | |
| 4,326,530 A * | 4/1982 | Fleury, Jr. .............. | A61B 18/14 606/47 |

(Continued)

FOREIGN PATENT DOCUMENTS

| | | | | |
|---|---|---|---|---|
| AU | 2500092 A * | 3/1993 | ........ | A61M 25/0905 |
| AU | 2006316567 B2 * | 1/2012 | ........... | A61M 25/09 |

(Continued)

OTHER PUBLICATIONS

International Search Report and Written Opinion in PCT Application No. PCT/IB2021/000087, dated Jun. 3, 2021 (8 pages).

(Continued)

*Primary Examiner* — Sean P Dougherty
(74) *Attorney, Agent, or Firm* — FINNEGAN, HENDERSON, FARABOW, GARRETT & DUNNER, LLP

(57) ABSTRACT

One embodiment of the present disclosure is directed to a selectively connectable medical device. The medical device may include a first flexible wire having an orifice on a distal end thereof and a flexible sleeve surrounding the first flexible wire. The flexible sleeve may be movable along the first flexible wire to a first orientation exposing the orifice, and a second orientation extending over the orifice. The device may further include a second flexible wire having a graspable region on an end thereof. The flexible sleeve may be configured, when the graspable region is threaded through the orifice, to be moved to the second orientation causing the graspable region to bend about an edge of the orifice, and to simultaneously cover the orifice and at least a portion of the graspable region, thereby locking the second wire to the first wire.

19 Claims, 3 Drawing Sheets

(56) References Cited

U.S. PATENT DOCUMENTS

| | | | | |
|---|---|---|---|---|
| 4,824,435 | A * | 4/1989 | Giesy | A61M 25/01 604/528 |
| 4,827,941 | A * | 5/1989 | Taylor | A61M 25/0905 600/585 |
| 4,875,489 | A * | 10/1989 | Messner | A61M 25/0905 604/528 |
| 5,109,867 | A | 5/1992 | Twyford, Jr. | |
| 5,813,405 | A * | 9/1998 | Montano, Jr. | A61M 25/0905 600/585 |
| 7,494,474 | B2 | 2/2009 | Richardson et al. | |
| 8,070,693 | B2 * | 12/2011 | Ayala | A61M 25/09033 600/585 |
| 2006/0047223 | A1 | 3/2006 | Grandfield et al. | |
| 2008/0051721 | A1 * | 2/2008 | Carter | A61M 25/09 604/164.13 |
| 2015/0051696 | A1 * | 2/2015 | Hou | A61M 25/0905 623/2.11 |
| 2017/0224953 | A1 * | 8/2017 | Tran | A61M 25/09 |
| 2018/0185618 | A1 | 7/2018 | Sweeney | |
| 2019/0192162 | A1 | 6/2019 | Lorenzo | |
| 2021/0046289 | A1 * | 2/2021 | McEvoy | A61M 25/0102 |

FOREIGN PATENT DOCUMENTS

| | | | | | |
|---|---|---|---|---|---|
| CN | 104244841 A | * | 12/2014 | | A61F 2/2457 |
| WO | WO-2007061702 A2 | * | 5/2007 | | A61M 25/0147 |
| WO | WO-2012096816 A1 | * | 7/2012 | | A61M 25/10 |

OTHER PUBLICATIONS

Chinese Patent Office, Office Action in CN App. No. 202180014866. 6, dated Sep. 4, 2025. (14 pages including machine translation).
European Patent Office, 4 Month Search Report in EP App. No. 21753901.4, dated Nov. 6, 2025. (7 pages).

* cited by examiner

FLEXIBLE SECURE CONNECTION OF MULTIPLE GUIDEWIRES

CROSS-REFERENCE TO RELATED APPLICATIONS

This application is a U.S. national phase entry under 35 U.S.C. § 371 from PCT International Application No. PCT/IB2021/000087, filed Feb. 16, 2021 which claims the benefit of priority of U.S. Provisional Patent Application No. 62/977,271, filed Feb. 16, 2020, the disclosure of each of which is hereby incorporated by reference in its entirety in the present application.

TECHNICAL FIELD

Some applications of the present disclosure relate to methods and devices for flexible secure connection of multiple guidewires. More specifically, some applications of the present disclosure relate to methods and devices for connecting guidewires in medical devices for transcatheter navigation within a body, such as the implantation of a transcatheter ventricular sling or papillary muscle sling.

BACKGROUND

In some transcatheter procedures, such as the implantation of a transcatheter ventricular sling or papillary muscle sling, it may be advantageous to be able to flexibly connect together multiple wires end to end. For example, in the case of the implantation of a transcatheter ventricular sling or papillary muscle sling, a wire is first placed through the ventricular trabeculae and then connected to another wire which is used to pull the implant into place. In this one exemplary application, the connected wires must be passed through the body.

Existing methods and devices for connecting guidewires end to end have a number of limitations that make them inapplicable for some transcatheter procedures, such as implantation of a transcatheter ventricular sling or papillary muscle sling. For example, some methods of connecting guidewire extensions are not secure enough to be used for passing the connected guidewires into the body, and are intended only for use during catheter exchange when the guidewire itself is not being manipulated, as manipulation of the guidewire could cause these types of connections to disconnect. Other types of guidewire connections are either too rigid or too large in diameter to be appropriate for the wires used in some transcatheter procedures, which may be as thin as 0.35 mm in diameter and must be flexible enough to pass smoothly through the ventricular anatomy. Additionally, in some procedures, it is necessary to grasp the distal end of a wire with a snare, pull it out of the body, and then attach that same distal end of the wire to the end of another wire.

Therefore, it would be advantageous to have a wire connection mechanism that may be configured to attach to the flexible end of a wire that is appropriate for being grasped.

SUMMARY

Presently disclosed embodiments recognize that a need exists for improved devices and methods for wire connection mechanisms in medical devices for transcatheter navigation to a cavity within the body. The embodiments of the present disclosure include methods and devices for the flexible connection of multiple guidewires in medical devices for transcatheter navigation to a cavity within the body, for example to a ventricle of a heart. Advantageously, some exemplary embodiments provide methods and devices for flexibly connecting multiple wires in a medical device end to end outside the body and then passing the wires through a lumen within the body.

Consistent with some embodiments of the present disclosure, a selectively connectable medical device is provided. The medical device may include a first flexible wire having an orifice on a distal end thereof and a flexible sleeve surrounding the first flexible wire. The flexible sleeve may be movable along the first flexible wire to a first orientation exposing the orifice, and a second orientation extending over the orifice.

In some embodiments, the device may further include a second flexible wire having a graspable region on an end thereof. The orifice of the first wire may be sized to permit the graspable region of the second wire to be threaded through the orifice when the orifice is exposed. The flexible sleeve may be configured, when the graspable region of the second flexible wire is threaded through the orifice, to be moved to the second orientation causing the graspable region of the second flexible wire to bend about an edge of the orifice, and to simultaneously cover the orifice of the first wire and at least a portion of the graspable region of the second wire, thereby locking the second wire to the first wire.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

DETAILED DESCRIPTION

Figure 1:
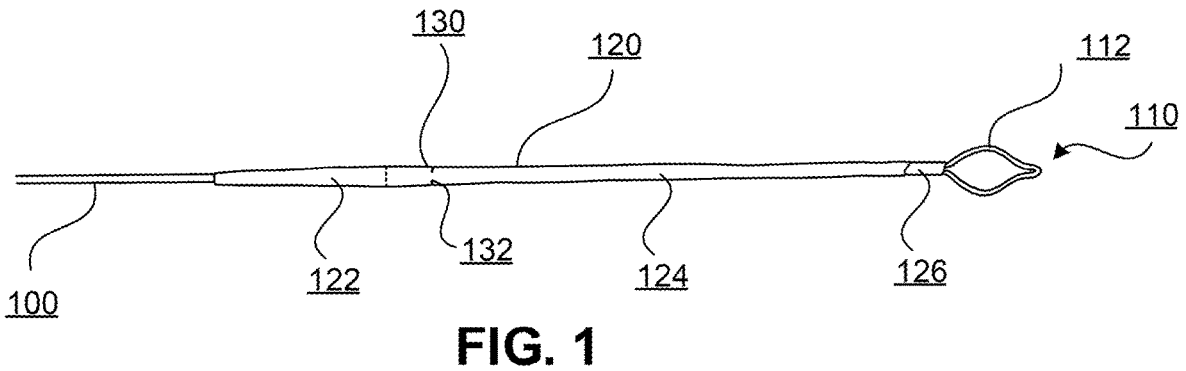
FIG. 1 illustrates an exemplary flexible wire with an orifice on a distal end thereof, consistent with some embodiments of the present disclosure.

The present disclosure relates to methods and devices for flexible secure connection of multiple guidewires. While the present disclosure provides examples of connecting guidewires in the context of the implantation of a transcatheter ventricular sling or papillary muscle sling, it should be noted that aspects of the disclosure in their broadest sense, are not limited to devices for implantation of a transcatheter ventricular sling or papillary muscle sling. Rather, it is contemplated that the forgoing principles may be applied to other devices for transcatheter navigation to any cavity within a body.

Exemplary embodiments are described with reference to the accompanying drawings. The figures are not necessarily drawn to scale. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

In the following description, various working examples are provided for illustrative purposes. However, is to be understood the present disclosure may be practiced without one or more of these details.

This disclosure is provided for the convenience of the reader to provide a basic understanding of a few exemplary embodiments and does not wholly define the breadth of the disclosure. This disclosure is not an extensive overview of all contemplated embodiments and is intended to neither identify key or critical elements of all embodiments nor to delineate the scope of any or all aspects. Its sole purpose is to present some features of one or more embodiments in a simplified form as a prelude to the more detailed description presented later. For convenience, the term "disclosed embodiments" or "exemplary embodiment" may be used herein to refer to a single embodiment or multiple embodiments of the disclosure.

Exemplary embodiments may include selectively connectable medical devices, consistent with the present disclosure. An exemplary selectively connectable medical device may include multiple flexible wires that may be selectively connected end to end. A flexible wire may be constructed of one or more flexible metal materials, such as stainless steel, cobalt-chrome alloy, titanium, and nickel-titanium alloy (nitinol). Additionally or alternatively, flexible wires and components thereof may also be constructed from one or more ceramics, polymers, composites, or any other biocompatible material. A flexible wire may refer to a single strand of material or a cable of multiple strands of material, such as a braided, twisted, or other arrangement of multiple strands.

In some embodiments, a selectively connectable medical device may include at least one first flexible wire and at least one second flexible wire that are selectively connectable and/or disconnectable. As discussed with reference to some exemplary embodiments below, a first metal wire and a second metal wire may be configured to engage each other at ends thereof to form or break a flexible connection. For example, a first flexible wire may include an orifice configured to engage a graspable region on a second flexible wire in order to connect the two wires. In some embodiments, the connection may be flexible enough for certain aspects of transcatheter navigation, such as passing smoothly through the ventricular anatomy or any other intraluminal movement.

Figure 2:
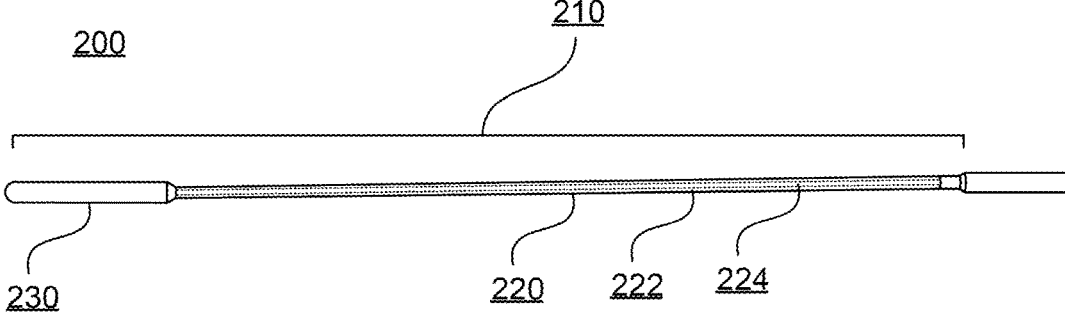
FIG. 2 illustrates an exemplary flexible wire having a graspable region on an end thereof, consistent with some embodiments of the present disclosure.

By way of example, FIG. 1 illustrates an exemplary flexible wire 100 having an orifice 112, and FIG. 2 illustrates an exemplary flexible wire 200 having a graspable region 210 on an end thereof, consistent with some embodiments of the present disclosure. As illustrated in FIGS. 3A-3E, flexible wire 100 and flexible wire 200 may be positioned in several configurations with respect to each other to selectively connect or disconnect from each other end to end.

Figure 3A:
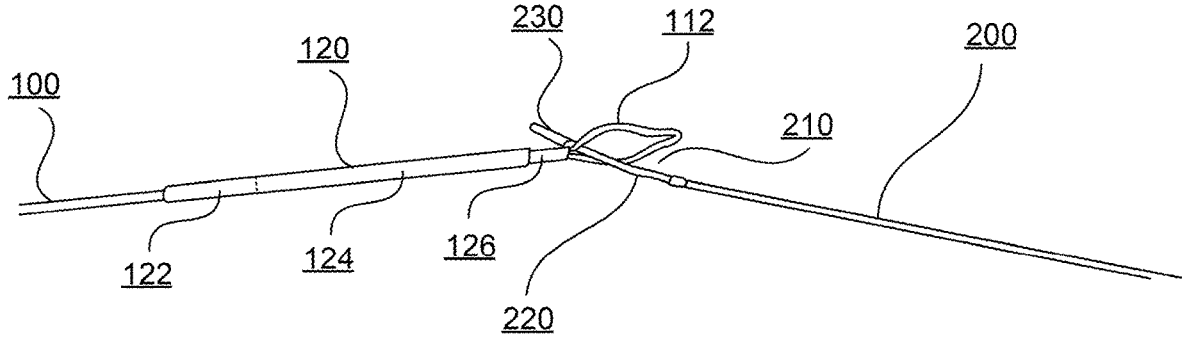
FIG. 3A illustrates a configuration of an exemplary selectively connectable medical device, consistent with some embodiments of the present disclosure.
Figure 3B:
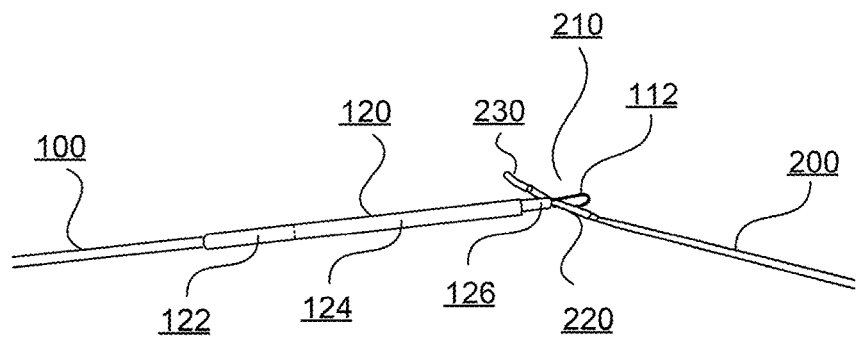
FIG. 3B illustrates another configuration of an exemplary selectively connectable medical device, consistent with some embodiments of the present disclosure.
Figure 3C:
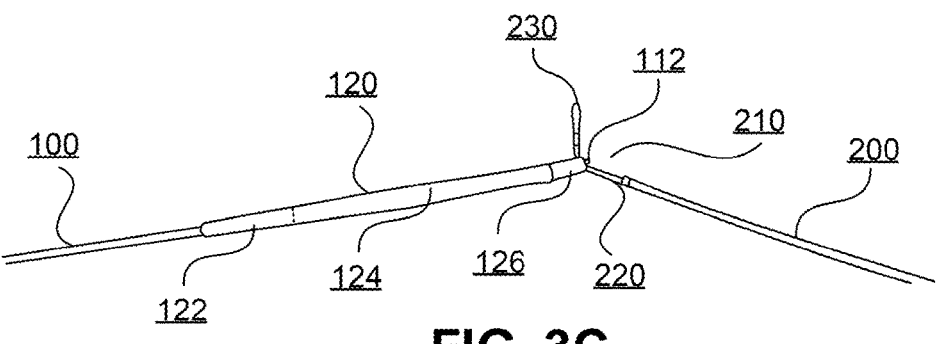
FIG. 3C illustrates another configuration of an exemplary selectively connectable medical device, consistent with some embodiments of the present disclosure.
Figure 3D:
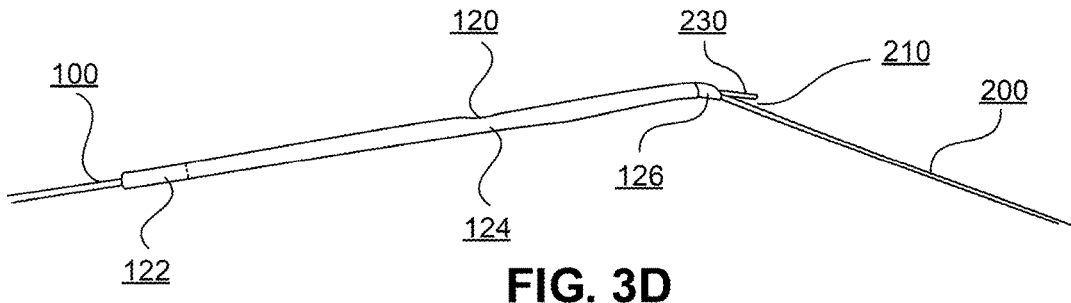
FIG. 3D illustrates another configuration of an exemplary selectively connectable medical device, consistent with some embodiments of the present disclosure.
Figure 3E:
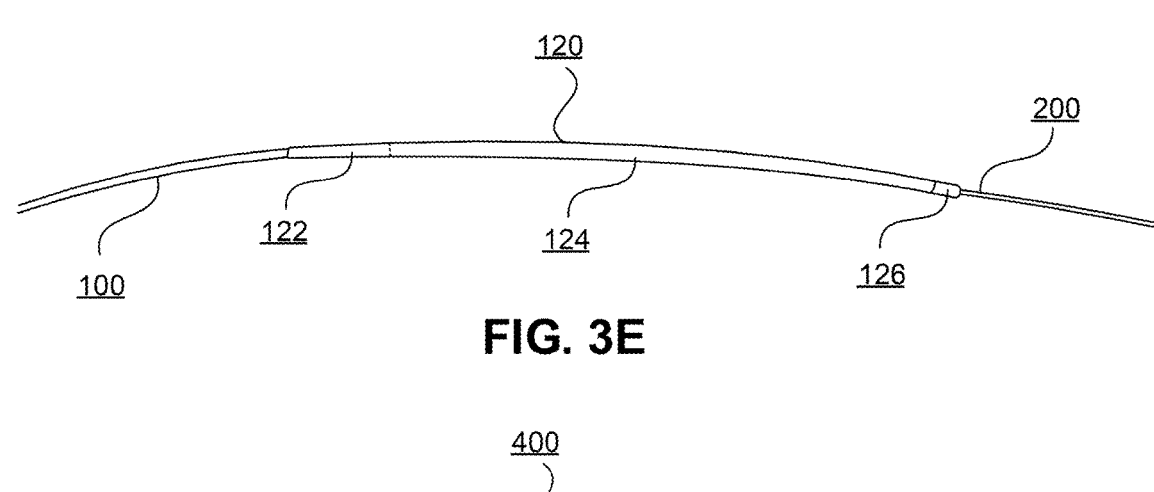
FIG. 3E illustrates another configuration of an exemplary selectively connectable medical device, consistent with some embodiments of the present disclosure.

An exemplary selectively connectable medical device may include a first flexible wire having an orifice on a distal end thereof. An orifice may be constructed from any biocompatible material and may be movable between an open and closed position, either through mechanical interaction and/or through the use of a pre-biased material such as an elastic metal or a shape memory alloy (e.g., nitinol). Although exemplary embodiments are discussed with reference to an orifice with a closed-loop configuration, it is to be understood that an orifice may include any open or closed configuration of biocompatible material movable between an open position and a closed position. By way of example, FIG. 1 illustrates an exemplary flexible wire 100 having an orifice 112 in an open position at a distal end 110 of flexible wire 100. FIGS. 3A-3E further illustrate orifice 112 in several configurations, with FIG. 3A depicting a configuration of flexible wires 100 and 200 with orifice 112 in a completely open configuration and FIG. 3E depicting a configuration of flexible wires 100 and 200 with orifice 112 (not shown) in a fully closed configuration and covered by flexible sleeve 120.

An exemplary selectively connectable medical device may include a flexible sleeve surrounding the first flexible wire. In some embodiments, the flexible sleeve may be movable along the first flexible wire to a first orientation exposing the orifice, and a second orientation extending over the orifice. The flexible sleeve and components thereof may be constructed of one or more metals, ceramics, polymers, composites, or any other biocompatible material, and may be in the form of a lumen with one or more inner diameters configured to fit over the first flexible wire and/or the orifice. In some embodiments, the flexible sleeve may be configured such that the inner diameter is smaller than a width of the orifice, such that when the flexible sleeve is moved in a distal direction relative to the first flexible wire, the flexible sleeve compresses the orifice to a closed position. In some embodiments, a length of the flexible sleeve may be less than half a length of the first flexible wire, although any length suitable for the intended use of disclosed medical devices may be used. By way of example, a length of the flexible sleeve may be less than 10 centimeters.

By way of example, FIGS. 3A-3E illustrate several orientations of flexible sleeve 120 with respect to flexible wires 100 and 200 that flexible sleeve 120 may be moved between. For example, FIG. 3A illustrates an orientation of flexible sleeve 120 in which flexible sleeve 120 covers a proximal portion of flexible wire 100 relative to orifice 112 while orifice 112 remains exposed. Alternatively, FIG. 3E illustrates an orientation of flexible sleeve 120 in which flexible sleeve 120 extends over both a portion of flexible wire 100 and orifice 112 such that orifice 112 is covered by flexible sleeve 120. When flexible sleeve 120 is moved from the orientation illustrated in FIG. 3A to the orientation illustrated in FIG. 3E, flexible sleeve 120 may exert a compressing force on orifice 112 such that orifice 112 moves from an open position to a closed position.

In some disclosed embodiments, the flexible sleeve may include a distal end region, a middle region, and a proximal region. In some embodiments, the inner diameters of the distal region and the proximal region may be smaller than an inner diameter of the middle region. For example, in some embodiments, the distal region and the proximal region may sit tighter against the first wire than the middle region due to their small inner diameters. By way of example, In FIG. 1 and FIGS. 3A-E, flexible sleeve 120 may include proximal region 122 and distal region 126 that have inner diameters that are smaller than the inner diameter of middle region 124.

In some disclosed embodiments, the flexible sleeve may have at least two regions having differing mechanical properties. For example, in some embodiments, a distal tip of the flexible sleeve may be made of a more elastic material than an adjacent region of the flexible sleeve to thereby enable the distal tip to stretch over the orifice and the flexible graspable region as the sleeve is moved from the first orientation to the second orientation. By way of example, as illustrated in FIG. 1 and FIGS. 3A-E, flexible sleeve 120 may include proximal region 122, middle region 124, and distal region or distal tip 126. Distal tip 126 may be constructed from a material that is more elastic than proximal region 122 and/or middle region 124. For example, an inner diameter of distal tip 126, when unstretched, may be smaller than a combined width of orifice 112, graspable region 210, and/or flexible wire 200. However, because distal tip 126 may be constructed of an elastic material such that, when stretched, its inner diameter may be increased, such that distal tip 126 stretches over orifice 112 and flexible graspable region 210 when flexible sleeve 120 is moved to the second orientation.

Figure 4:
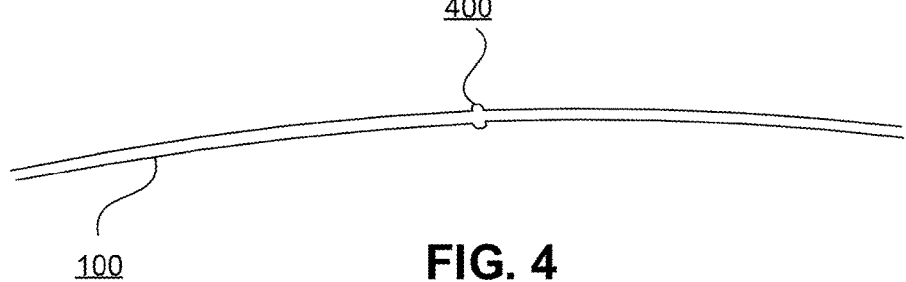
FIG. 4 illustrates an exemplary flexible wire including a protrusion thereon, consistent with some embodiments of the present disclosure.

In some disclosed embodiments, the first flexible wire may include at least one protrusion thereon configured for location within the middle region of the sleeve. A protrusion may refer to a portion of the first flexible wire that has an outer diameter different than a diameter of the first flexible wire, and may be located on the flexible wire in a proximal location with respect to the orifice. The protrusion may be included as part of the first flexible wire, or it may be attached to the first flexible wire as an additional component. The protrusion may have an outer diameter smaller than the inner diameter of the middle region of the flexible sleeve and larger than the inner diameters of the proximal region and the distal region. In some embodiments, such a configuration may at least partially impede the proximal region of the flexible sleeve from moving distally past the protrusion or the distal region of the flexible sleeve from moving proximally past the protrusion. By way of example, FIG. 4 illustrates an exemplary first flexible wire 100 having a protrusion 400 thereon.

In some disclosed embodiments, the flexible sleeve may include a lock configured to secure the sleeve in the second orientation. A lock may refer to a mechanism, such as one or more protrusions or components located on an inner surface of the flexible sleeve, that is configured to interact with the first flexible wire to lock the flexible sleeve in place with respect to the first flexible wire. In some embodiments, the lock may be configured to engage with a protrusion on the first flexible wire to secure the sleeve in the second orientation. By way of example, in FIG. 1, lock 130 may be located on an inner portion of flexible sleeve 120 and may be configured to engage with protrusion 400 (not shown) in order to secure flexible sleeve 120 in place.

In some disclosed embodiments, the lock may include at least one elastic prong protruding inwardly from the flexible sleeve. The at least one elastic prong, for example, may be configured to pass over a protrusion on the first flexible wire and to become engaged with a distal side of the protrusion when the sleeve is moved to the second orientation, thereby preventing proximal movement of the flexible sleeve. The elastic prong may be included as part of the flexible sleeve, or it may be attached to the flexible sleeve as an additional component. By way of example, in FIG. 1, lock 130 may include at least one elastic prong 132. The elastic prong may be made of plastic, metal, or another suitable material. The elasticity and mechanical configuration of elastic prong 112 may be such that lock 130 may pass over protrusion 400 (not shown) of flexible wire 100 in a distal direction but may not pass over protrusion 400 in a proximal direction. Thus, when lock 130 passes over protrusion 400 in a distal direction, it prevents proximal movement of flexible sleeve 120.

In some disclosed embodiments, the orifice may be selectively adjustable between an open position and a closed position, and is biased to the open position. For example, as discussed above, the orifice may be constructed of pre-biased material such as an elastic metal or a shape memory alloy (e.g., nitinol) such that the orifice is biased to a shape corresponding to the open position. In some embodiments, the flexible sleeve may be configured to enable the orifice to expand to the open position when the flexible sleeve is in the first orientation and to compress the orifice to the closed position when the flexible sleeve is moved from the first orientation to the second orientation. As discussed above, in some embodiments, the flexible sleeve may exert a compressing force on the orifice at least due an inner diameter of the flexible sleeve being smaller than a width of the orifice. In some embodiments, the orifice may be a compressible wire loop, although other configurations are also possible. The compressible wire loop may be formed from a single wire or a twisted or braided cable. The compressible wire loop may be formed from metal, polymer, or any other biocompatible wire having appropriate tensile strength and flexibility.

By way of example, FIGS. 3A-3E illustrate several orientations of flexible sleeve 120 with respect to flexible wires 100 and 200 that flexible sleeve 120 may be moved between. For example, in FIG. 3A illustrates an orientation of flexible sleeve 120 in which flexible sleeve 120 covers a proximal portion of flexible wire 100 relative to orifice 112 while orifice 112 remains exposed. In some embodiments, orifice 112 is a compressible wire loop in an open position in FIG. 3A because it is biased to the open position. In FIG. 3E, however, orifice 112 is covered by flexible sleeve 120 and is thus compressed to a closed position. For example, when flexible sleeve 120 is moved from the orientation illustrated in FIG. 3A to the orientation illustrated in FIG. 3E, flexible sleeve 120 may exert a compressing force on orifice 112 such that orifice 112 is prevented from having the pre-biased open position.

An exemplary selectively connectable medical device may include a second flexible wire having a graspable region on an end thereof. A graspable region may refer to a portion of the second flexible wire that is configured to engage the orifice of the first flexible wire in order to form a connection between the first flexible wire and the second flexible wire. For example, in some embodiments, the orifice of the first wire may be sized to permit the graspable region of the second wire to be threaded through the orifice when the orifice is exposed. By way of example, FIG. 2 illustrates an exemplary flexible wire 200 having a graspable region 210 on an end thereof. As illustrated in FIG. 3A, orifice 112 of flexible wire 100 is sized to permit at least a portion of graspable region 210 to be threaded through orifice 112.

In some disclosed embodiments, the graspable region may include at least one of a stainless-steel cable, a nitinol wire, a nitinol cable, and a radiopaque material. The graspable region may be entirely constructed from at least one of these components and/or materials, or it may be constructed from several regions and/or components that are each constructed from one or more combinations of these components and/or materials. For example, the graspable region of the second flexible wire may include an inner metal core and an outer coil of radiopaque material. The inner metal core may be constructed, for example, from a stainless-steel cable, a nitinol wire, and/or a nitinol cable, while an outer portion of the graspable region may be constructed from at least one radiopaque material and/or a coil of radiopaque material. By way of example. FIG. 2 illustrates an exemplary flexible wire 200 having a graspable region 210 on an end thereof. In some embodiments, graspable region 210 may include an inner metal core 224 that may be constructed from a stainless-steel cable, a nitinol wire, and/or a nitinol cable, and an outer portion 222 that may be constructed from a radiopaque material and/or a coil of radiopaque material.

An exemplary flexible sleeve of the present disclosure may be configured, when the graspable region of the second flexible wire is threaded through the orifice, to be moved to the second orientation causing the graspable region of the second flexible wire to bend about an edge of the orifice, and to simultaneously cover the orifice of the first wire and at least a portion of the graspable region of the second wire, thereby locking the second wire to the first wire. In some embodiments, the flexible graspable region may be configured to be bent by the sleeve as the sleeve is pushed distally over the orifice. For example, the flexible sleeve may push portions of the graspable region against a distal edge of the orifice when the flexible sleeve moves towards the second configuration, thereby forcing the graspable region to bend. In some embodiments, the flexible sleeve may be configured to cover an entirety of the graspable region in the second orientation, although it is also possible that the sleeve may be configured to cover only a portion of the graspable region in the second orientation.

By way of example, FIGS. 3A-E illustrate several configurations of flexible wire 100 and flexible wire 200 wherein flexible sleeve 120 is positioned in several orientations. In FIG. 3A, the flexible sleeve 120 is in a first orientation in which orifice 112 is exposed and in which graspable region 210 has been threaded through the orifice. As flexible sleeve 120 moves toward a second position in FIGS. 3B and 3C, orifice 112 and flexible sleeve 120 exert opposing forces on portions of graspable region 210, thereby causing graspable region 210 to bend back on itself. In some embodiments, FIG. 3D may correspond to the second orientation of flexible sleeve 120 in which only a portion of graspable region 210 is covered by flexible sleeve 120. Additionally or alternatively, however, FIG. 3E may correspond to the second orientation of flexible sleeve 120 in which the entirety of graspable region 210 (not shown) is covered by flexible sleeve 120.

In some disclosed embodiments, the distal tip of the flexible sleeve may have an inner diameter less than or equal to a diameter of the second flexible wire such that when the flexible sleeve is in the second orientation, the distal tip engages the second wire. The distal tip may engage the wire, for example, by fitting tightly and/or forming a seal against an outer portion of the second flexible wire due to the inner diameter of the distal tip being less than or equal to a diameter of the second flexible wire. By way of example, FIG. 3E illustrates a configuration of flexible wire 100 and flexible wire 200 wherein a distal tip 126 of flexible region 120 engages flexible wire 200.

In some embodiments, an exemplary graspable region may include a locking element proximate an end of the graspable region, wherein the locking element is configured to render rigid a distal region of the flexible graspable region. A locking element may refer to any portion or element of the graspable region with certain mechanical and/or geometric properties configured to facilitate the engagement of the orifice of the first flexible wire and the graspable region of the second flexible wire. For example, in some embodiments, a diameter of the highly flexible portion of the graspable region may be less than a diameter of a rigid locking element on a distal end of the graspable region, such that distal movement of the orifice with respect to the graspable region is at least partially impeded by the rigid locking element having a larger diameter than the highly flexible portion. In some disclosed embodiments, diameters of the graspable region and/or the locking element may be less than or equal to a diameter of the second wire. In some disclosed embodiments, an axial length of the region rendered rigid is greater than a largest inner diameter of the flexible sleeve.

By way of example, FIG. 2 illustrates an exemplary flexible wire having a graspable region 210 on an end thereof, in which graspable region 210 includes a highly flexible portion 220 and a distal rigid locking element 230. Highly flexible portion 220 may have a diameter less than a diameter of rigid distal locking element 230 such that distal movement of orifice 112 with respect to graspable region 210 is prevented, as illustrated in FIG. 3C, for example. Although not illustrated herein, the graspable region may have other geometric and/or mechanical properties suitable for facilitating the engagement of the orifice of the first flexible wire and the graspable region that fall within the scope of the present disclosure. For example, additionally or alternatively, graspable region 210 may include a coil or may be constructed of a material that may impede distal movement of orifice 112 through friction or another form of adhesion when orifice 112 becomes engaged with graspable region 210.

Disclosed embodiments may include any one of the following bullet-pointed features alone or in combination with one or more other bullet-pointed features, whether implemented as a method, device, or system:
  a selectively connectable medical device;
  a first flexible wire having an orifice on a distal end thereof;
  a flexible sleeve surrounding the first flexible wire, the flexible sleeve being movable along the first flexible wire to a first orientation exposing the orifice, and a second orientation extending over the orifice;
  a second flexible wire having a graspable region on an end thereof;
  wherein the orifice of the first wire is sized to permit the graspable region of the second wire to be threaded through the orifice when the orifice is exposed;
  wherein the flexible sleeve is configured, when the graspable region of the second flexible wire is threaded through the orifice, to be moved to the second orientation causing the graspable region of the second flexible wire to bend about an edge of the orifice, and to simultaneously cover the orifice of the first wire and at least a portion of the graspable region of the second wire, thereby locking the second wire to the first wire;

wherein the orifice is selectively adjustable between an open position and a closed position, and is biased to the open position;

wherein the flexible sleeve is configured to enable the orifice to expand to the open position when the sleeve is in the first orientation and to compress the orifice to the closed position when the sleeve is moved from the first orientation to the second orientation;

a locking element proximate an end of the graspable region, wherein the locking element is configured to render rigid a distal region of the flexible graspable region;

wherein diameters of each of the graspable region and the locking element are less than or equal to a diameter of the second wire;

wherein an axial length of the region rendered rigid is greater than a largest inner diameter of the flexible sleeve;

wherein the first flexible wire and the second flexible wire are selectively connectable and disconnectable;

wherein a length of the flexible sleeve is less than half a length of the first flexible wire;

wherein the orifice is a compressible wire loop;

wherein a length of the flexible sleeve is less than 10 centimeters;

wherein the flexible sleeve includes a distal end region, a middle region, and a proximal region;

wherein inner diameters of the distal region and the proximal region are smaller than an inner diameter of the middle region;

wherein the first flexible wire further includes a protrusion thereon configured for location within the middle region of the sleeve, the protrusion having an outer diameter smaller than the inner diameter of the middle region and larger than the inner diameters of the proximal region and the distal region;

wherein the flexible sleeve includes a lock configured to secure the sleeve in the second orientation;

wherein the lock includes at least one elastic prong protruding inwardly from the flexible sleeve, the at least one elastic prong being configured to pass over a protrusion on the first flexible wire and to become engaged with a distal side of the protrusion when the sleeve is moved to the second orientation, thereby preventing proximal movement of the flexible sleeve;

wherein the flexible sleeve has at least two regions having differing mechanical properties;

wherein a distal tip of the flexible sleeve is made of a more elastic material than an adjacent region of the flexible sleeve to thereby enable the distal tip to stretch over the orifice and the flexible graspable region as the sleeve is moved from the first orientation to the second orientation;

wherein the distal tip of the flexible sleeve has an inner diameter less than or equal to a diameter of the second flexible wire such that when the flexible sleeve is in the second orientation, the distal tip engages the second wire;

wherein the flexible sleeve is configured, in the second orientation, to cover an entirety of the graspable region;

wherein the flexible graspable region is configured to be bent by the sleeve as the sleeve is pushed distally over the orifice;

wherein the graspable region of the second wire includes a radiopaque material;

wherein the graspable region of the second wire includes an inner metal core and an outer coil of radiopaque material; and, wherein the graspable region includes at least one of a stainless-steel cable, a nitinol wire and a nitinol cable.

While the present disclosure is described herein with reference to illustrative embodiments of devices used for particular applications, such as for navigation through a ventricle of a heart for cardiac repair, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A selectively connectable medical device, comprising:
a first flexible wire having an orifice on a distal end thereof;
a flexible sleeve surrounding the first flexible wire, the flexible sleeve being movable along the first flexible wire to a first orientation exposing the orifice, and a second orientation extending over the orifice;
a second flexible wire having a flexible graspable region on an end thereof, wherein the orifice of the first wire is sized to permit the flexible graspable region of the second wire to be threaded through the orifice when the orifice is exposed, and wherein the flexible sleeve is configured, when the flexible graspable region of the second flexible wire is threaded through the orifice, to be moved to the second orientation causing the flexible graspable region of the second flexible wire to bend about an edge of the orifice, and to simultaneously cover the orifice of the first wire and at least a portion of the flexible graspable region of the second wire, thereby locking the second wire to the first wire; and
a flexible wire locking element proximate an end of the flexible graspable region, wherein the flexible wire locking element is configured to render rigid a distal region of the flexible graspable region.

2. The device of claim 1, wherein the orifice is selectively adjustable between an open position and a closed position, and is biased to the open position, and wherein the flexible sleeve is configured to enable the orifice to expand to the open position when the sleeve is in the first orientation and to compress the orifice to the closed position when the sleeve is moved from the first orientation to the second orientation.

3. The device of claim 1, wherein diameters of each of the flexible graspable region and the flexible wire locking element are less than or equal to a diameter of the second wire.

4. The device of claim 1, wherein an axial length of the region rendered rigid is greater than a largest inner diameter of the flexible sleeve.

5. The device of claim 1, wherein the first flexible wire and the second flexible wire are selectively connectable and disconnectable.

6. The device of claim 1, wherein a length of the flexible sleeve is less than half a length of the first flexible wire.

7. The device of claim 2, wherein the orifice is a compressible wire loop.

8. The device of claim 1, wherein a length of the flexible sleeve is less than 10 centimeters.

9. The device of claim 1, wherein the flexible sleeve includes a distal end region, a middle region, and a proximal region, wherein inner diameters of the distal region and the proximal region are smaller than an inner diameter of the middle region, and wherein the first flexible wire further includes a protrusion thereon configured for location within the middle region of the sleeve, the protrusion having an outer diameter smaller than the inner diameter of the middle region and larger than the inner diameters of the proximal region and the distal region.

10. The device of claim 1, wherein the flexible sleeve includes a lock configured to secure the sleeve in the second orientation.

11. The device of claim 10, wherein the lock includes at least one elastic prong protruding inwardly from the flexible sleeve, the at least one elastic prong being configured to pass over a protrusion on the first flexible wire and to become engaged with a distal side of the protrusion when the sleeve is moved to the second orientation, thereby preventing proximal movement of the flexible sleeve.

12. The device of claim 1 wherein the flexible sleeve has at least two regions having differing mechanical properties.

13. The device of claim 12, wherein a distal tip of the flexible sleeve is made of a more elastic material than an adjacent region of the flexible sleeve to thereby enable the distal tip to stretch over the orifice and the flexible graspable region as the sleeve is moved from the first orientation to the second orientation.

14. The device of claim 13, wherein the distal tip of the flexible sleeve has an inner diameter less than or equal to a diameter of the second flexible wire such that when the flexible sleeve is in the second orientation, the distal tip engages the second wire.

15. The device of claim 6, wherein the flexible sleeve is configured, in the second orientation, to cover an entirety of the flexible graspable region.

16. The device of claim 1, wherein the flexible graspable region is configured to be bent by the sleeve as the sleeve is pushed distally over the orifice.

17. The device of claim 1, wherein the flexible graspable region of the second wire includes a radiopaque material.

18. The device of claim 17, wherein the flexible graspable region of the second wire includes an inner metal core and an outer coil of radiopaque material.

19. The device of claim 1, wherein the flexible graspable region includes at least one of a stainless-steel cable, a nitinol wire, and a nitinol cable.

\* \* \* \* \*